(12) United States Patent
Ritter, III et al.

(10) Patent No.: US 9,737,679 B2
(45) Date of Patent: Aug. 22, 2017

(54) AUTOMATED HME WITH NEBULIZER CONNECTION

(71) Applicant: MERCURY ENTERPRISES, INC., Clearwater, FL (US)

(72) Inventors: James Russell Ritter, III, Largo, FL (US); Jeffrey B. Ratner, Pinellas Park, FL (US); Mark Fergason, Sarasota, FL (US)

(73) Assignee: MERCURY ENTERPRISES, INC, Clearwater, FL (US)

( * ) Notice: Subject to any disclaimer, the term of this patent is extended or adjusted under 35 U.S.C. 154(b) by 743 days.

(21) Appl. No.: 14/291,108

(22) Filed: May 30, 2014

(65) Prior Publication Data

US 2015/0343164 A1 Dec. 3, 2015

(51) Int. Cl.
*A61M 16/08* (2006.01)
*A61M 16/10* (2006.01)
*A61M 16/01* (2006.01)
*A61M 11/00* (2006.01)

(52) U.S. Cl.
CPC ........ *A61M 16/0816* (2013.01); *A61M 16/01* (2013.01); *A61M 16/1045* (2013.01); *A61M 11/00* (2013.01); *A61M 16/104* (2013.01); *A61M 16/1055* (2013.01)

(58) Field of Classification Search
CPC .............. A61M 16/1045; A61M 16/10; A61M 16/105; A61M 16/1065; A61M 16/106; A61M 16/1075; A61M 16/108; A61M 16/1085; A61M 16/109; A61M 16/1095; A61M 16/14; A61M 16/16; A61M 16/18; A61M 16/20; A61M 16/201; A61M 16/206

See application file for complete search history.

(56) References Cited

U.S. PATENT DOCUMENTS

| 5,035,236 | A | 7/1991 | Kanegaonkar |
| 5,546,930 | A | 8/1996 | Wikefeldt |
| 6,095,135 | A | 8/2000 | Clawson et al. |
| 6,550,476 | B1 * | 4/2003 | Ryder ............... A61M 16/1045 128/201.13 |
| 6,588,421 | B1 | 7/2003 | Diehl et al. |
| 6,609,515 | B2 | 8/2003 | Bienvenu et al. |
| 6,792,946 | B1 * | 9/2004 | Waldo, Jr. ......... A61M 16/1045 128/201.13 |

(Continued)

*Primary Examiner* — Justine Yu
*Assistant Examiner* — Michael Tsai
(74) *Attorney, Agent, or Firm* — Larson & Larson, P.A.; Frank Liebenow

(57) ABSTRACT

An airway circuit has two modes of operation, dependent upon the presence or absence of a nebulizer in a nebulizer port. When the nebulizer if absent, a patient port is in fluid communications with a ventilation circuit port through a heat and humidity exchange element. When the nebulizer is inserted into the nebulizer port, the nebulizer port (and nebulizer), patient port, and ventilation circuit port are in fluid communications with each other and the heat and humidity exchange element is isolated, thereby protecting the heat and humidity exchange element from medicines emanating from the nebulizer. After the nebulizer is removed from the nebulizer port, the patient port is again placed in fluid communications with the ventilation circuit port through a heat and humidity exchange element.

4 Claims, 5 Drawing Sheets

(56) References Cited

U.S. PATENT DOCUMENTS

| | | |
|---|---|---|
| 7,594,509 B2 | 9/2009 | Burk |
| 7,624,731 B2 * | 12/2009 | Walstrom .......... A61M 15/0086 |
| | | 128/201.13 |
| 2004/0123974 A1 * | 7/2004 | Marler .................. A61M 16/08 |
| | | 165/9.4 |
| 2013/0068219 A1 * | 3/2013 | Collazo ............. A61M 16/1045 |
| | | 128/201.13 |

* cited by examiner

US 9,737,679 B2

AUTOMATED HME WITH NEBULIZER CONNECTION

FIELD

This invention relates to the field of patient connectors intended for connecting a patient to a respirator and/or to an anesthesia device. More particularly, the present invention relates to a patient connector that includes a heat and moisture exchange device that is isolated from the circuit when the nebulizer is attached.

BACKGROUND

Patient connectors are generally used for connecting patients to respirators, anesthesia devices, etc. When a patient is interfaced to such respirators and/or anesthesia devices, often the air that the patient breathes in is very dry and often cool. To reduce the negative effects of breathing this cool, dry air, prior patient connectors often include in-line heat and moisture exchange devices (HME devices). Heat and moisture exchange devices capture heat and moisture when the patient exhales and returns the heat and moisture to the patient when the patient inhales. As the patent exhales, the patient's breath is very humid and warm and this heat and humidity is captured in the HME and the heat and humidity is released when the patient inhales, making the air that the patient inhales warmer and more humid. Unfortunately, the actual membrane used is the heat and moisture exchange is not compatible with medicines. Typically, patients are administered medicine with the help of a nebulizer which finely divides the medicine into fine droplets which are inhaled. If a nebulizer is used in conjunction with a heat and moisture exchange device, exposure of the heat and moisture exchange element to the medication will impact the operation of the heat and moisture exchange element and possibly permanently damage the heat and moisture exchange element.

In the past, heat and moisture exchange devices had to be removed from the circuit when the patient is given medicine by way of a nebulizer. This method suffered from the complexity of rearranging the airway circuit during the administration of the medicine, then reconnecting the airway circuit and the time lag in which the circuit is disconnected.

Some circuits introduced the output of the nebulizer downstream, away from the heat and moisture exchange element as in U.S. Pat. No. 5,546,930 issued on Aug. 20, 1996. In this, a long tube separates the heat and moisture exchange element from the medicine injection point and a manually removable cap covers the port in which the nebulizer is removably attached. In this type of circuit, after the patient inhales some air mixed with nebulized medication, some amount of nebulized medication remains in the patient's airways and in the patient end of this circuit and, upon exhaling, some of this nebulized medication flows through a second leg of the circuit and into the heat and moisture exchange element, which is not desired.

Recognizing this issue, other devices have a knob, valve, or switch which initiates bypass of the heat and moisture exchange element. One such example is U.S. Pat. No. 7,594,509, issued Sep. 29, 2009. The problem with a manual function that bypasses the heat and moisture exchange element is that a busy caregiver must remember to re-enable the heat and moisture exchange element after the medication is administered, which does not always happen and, the results of such are often not readily know, so the patient starts feeling discomfort after the caregiver has left the patients proximity. Additionally, it is easy for the caregiver to forget to bypass the heat and moisture exchange element and administer the medication while the heat and moisture exchange element is in the circuit, leading to future problems with the heat and moisture exchange element and a potential reduction in the medication administered to the patient, as some of the medication becomes trapped in the heat and moisture exchange element.

What is needed is a circuit that will automatically remove the heat and moisture exchange element while the nebulizer is attached to the circuit.

SUMMARY

In one embodiment, a patient connector providing heat and humidity exchange is disclosed including an enclosure having a patient port for connection to a patient circuit, a vent communications port for connection to a ventilation circuit, and a nebulizer port for intermittent connection to a nebulizer. Internal to the enclosure is a heat and moisture exchange element. A mechanism fluidly connects the patient port through the heat and moisture exchange element to the vent communications port when the nebulizer port is empty; and the mechanism fluidly connecting the patient port to the vent communications port and to the nebulizer port when the nebulizer port is occupied, thereby isolating the heat and moisture exchange element from the circuit until the nebulizer port is again vacant.

In another embodiment, a patient connector providing heat and humidity exchange is disclosed including an enclosure having a patient port for connection to a patient circuit, a vent communications port for connection to a ventilation circuit, and a nebulizer port for intermittent connection to a nebulizer. A heat and moisture exchange element holder secured within the enclosure has a heat and moisture exchange element contained there within, an upper port in fluid communication with a first side of the heat and moisture exchange element and a lower port in fluid communication with an opposing side of the heat and moisture exchange element. There is a device for urging that urges the heat and moisture exchange element holder towards the nebulizer port and a linkage between the nebulizer port and the heat and moisture exchange element. The linkage blocks the nebulizer port, the patient port is in fluid communications with the upper port, and the vent communications port is in fluid communications with the lower port allowing fluid communications between the patient port and the vent communications port through the heat and moisture exchange element until insertion of a nebulizer into the nebulizer port. After insertion of a nebulizer into the nebulizer port, the linkage opens the nebulizer port, the patient port is placed in fluid communications with the nebulizer port and the vent communications port allowing fluid communications between the patient port and the vent communications port and the nebulizer port until the nebulizer is removed from the nebulizer port.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION

Figure 1:
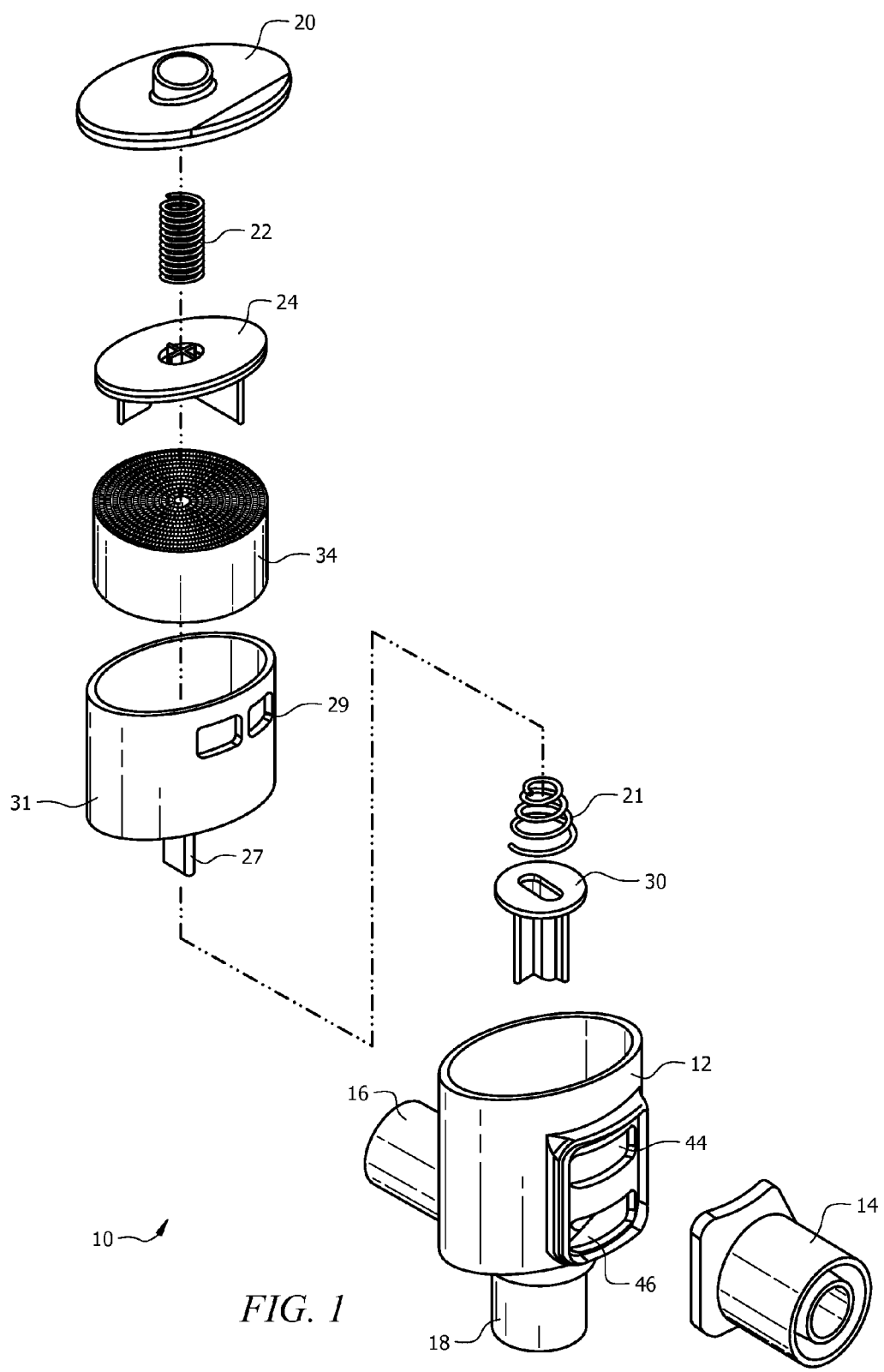
FIG. 1 illustrates an exploded view of an exemplary airway circuit with heat and moisture exchange element.

Reference will now be made in detail to the presently preferred embodiments of the invention, examples of which are illustrated in the accompanying drawings. Throughout the following detailed description, the same reference numerals refer to the same elements in all figures.

Although a specific embodiment of the invention is shown in the drawings and used in the description, there is no limitation to any specific design or structure as long as, upon insertion of the nebulizer, the heat and moisture exchange element is isolated from the breathing circuit and upon removal of the nebulizer, the heat and moisture exchange element is placed back into the circuit.

Referring to FIG. 1, an exploded view of an exemplary airway circuit 10 with heat and moisture exchange element 34 is shown. In this exemplary airway circuit 10, the patient port 14 is for connecting to, for example, tubes that communicate with the patient's airways, orally, nasally, or through a tracheotomy. A vent circuit communications port 16 is for connection to any ventilation source known in the medical industry. The nebulizer port 18 is for intermittent connection to a nebulizer when medication needs to be administered to a patient that is connected to the patient port 14. A heat and moisture exchange element holder 31 fits within an enclosure 12 and is allowed to move up/down along an axis of, for example, the nebulizer port 18. A cap 20 seals the enclosure 12, maintaining the heat and moisture exchange element holder 31 within the enclosure 12. A heat and moisture exchange element holder lid 24 maintains the heat and moisture exchange element 34 within the heat and moisture exchange element holder 31. A main spring 22 urges the heat and moisture exchange element holder 31 into the air circuit, communicating gas flow between the vent circuit communications port 16 and the patient port 14, through the heat and moisture exchange element 34. A nebulizer insertion linkage 30 interfaces with the secondary spring 21. As will be shown, when a nebulizer 50 (see FIGS. 2 and 3) is inserted into the nebulizer port 18, the nebulizer insertion linkage 30 is displaced by an end of the nebulizer 50, pushing the secondary spring 21 and, hence, the heat and moisture exchange element holder 31 upward (away from the nebulizer port 18) and out of the circuit. With the nebulizer 50 inserted, the heat and moisture exchange element 34 is out of the circuit and gas flows between the vent circuit communications port 16, the nebulizer port 18 and the patient port 14, while isolating the heat and moisture exchange element 34.

To maintain position and prevent rotation of the heat and moisture exchange element holder 31, a key 27 mates with a mating hole in the nebulizer insertion linkage 30. Note that the upper port of the heat and moisture exchange element holder 31 aligns with the upper enclosure port 44 when the heat and moisture exchange element holder 31 rests on the bottom of the enclosure 12 (e.g. urged to the bottom by the main spring 22) and the lower enclosure port 44 is occluded by a surface of the heat and moisture exchange element holder 31. In some embodiments, the insertion linkage 30 is keyed for the nebulizer port 18.

Figure 2:
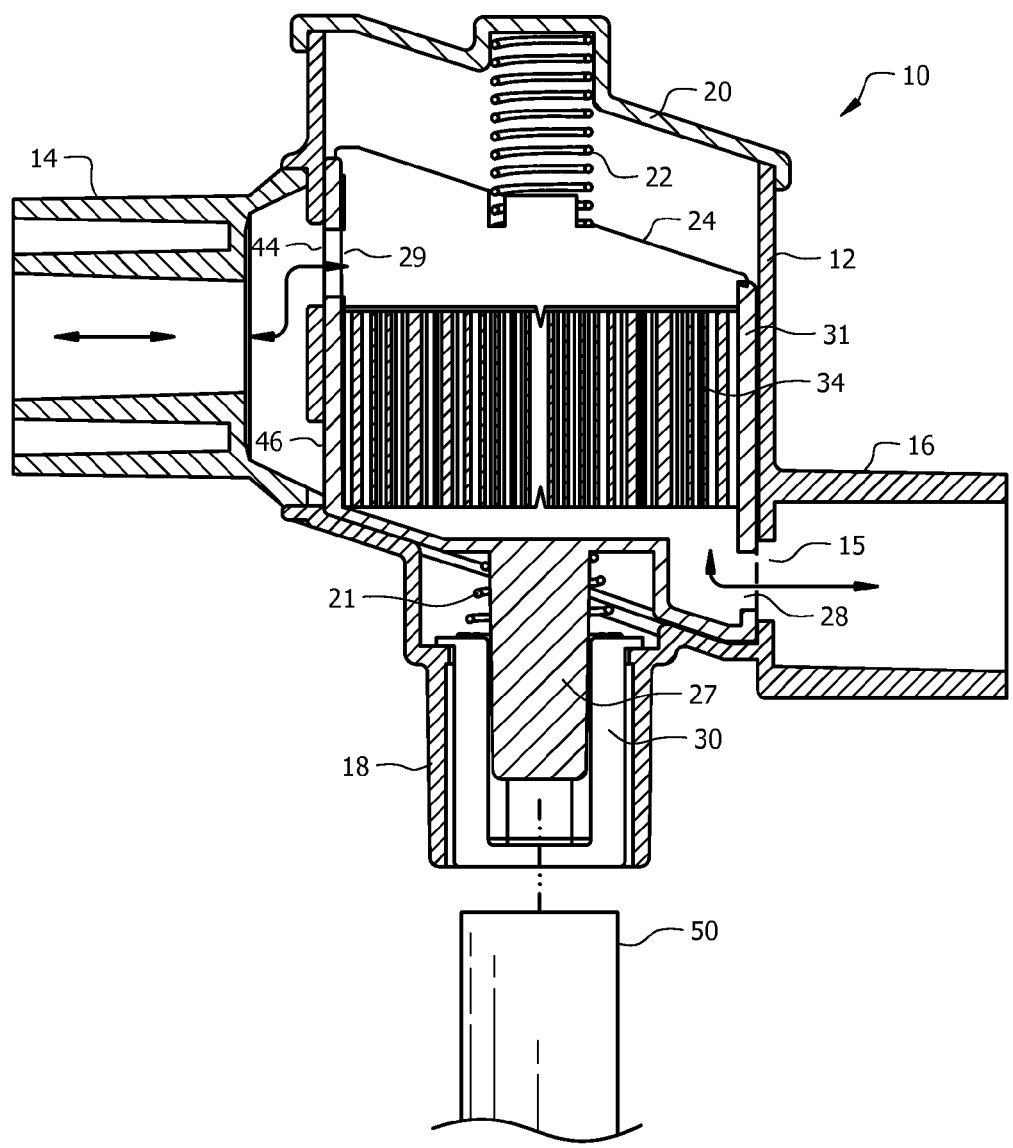
FIG. 2 illustrates a cross sectional view of the exemplary airway circuit with the heat and moisture exchange element in the circuit.
Figure 3:
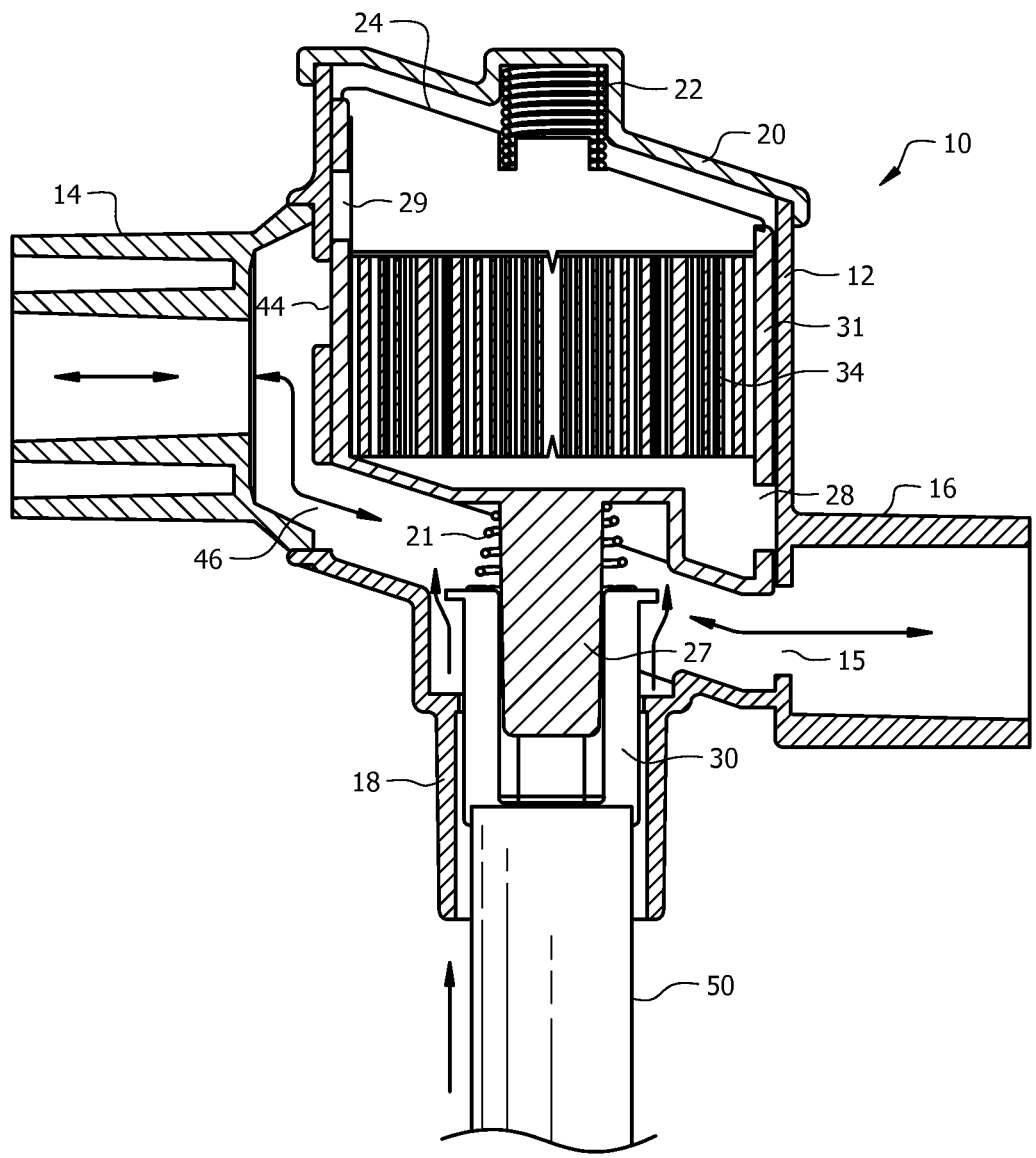
FIG. 3 illustrates a cross sectional view of the exemplary airway circuit with the heat and moisture exchange element isolated from the circuit.

Referring to FIGS. 2 and 3, cross sectional views of the exemplary airway circuit 10 are shown. In FIG. 2, the nebulizer 50 is absent and the heat and moisture exchange element 34 is within the air path. In FIG. 3, the nebulizer 50 is inserted and the heat and moisture exchange element 34 is consequently isolated from the air path.

In FIG. 2, there is no nebulizer 50 inserted into the nebulizer port 18 (a nebulizer 50 is shown ready for insertion). Therefore, gases communicate between the patient port 14 through the upper enclosure port 44, the upper port 29 of the heat and moisture exchange element holder 31, the heat and moisture exchange element 34, a lower port 28 of the heat and moisture exchange element holder 31, a lower vent port 15 of the housing, and the vent circuit communication port 16. The main spring 22 urges the heat and moisture exchange element holder 31 to rest on the bottom of the enclosure 12, while the secondary spring 21 urges the nebulizer insertion linkage 30 away from the heat and moisture exchange element holder 31, seating the nebulizer insertion linkage 30 against the edges of the nebulizer port 18, thereby preventing/reducing flow of gases in/out of the nebulizer port 18.

In FIG. 3, the nebulizer 50 has been inserted into the nebulizer port 18. The main spring 22 gives way to the displacement of the nebulizer 50 and the heat and moisture exchange element holder 31 moves upward (toward the cap 20, upward with respect the FIG. 3) until the heat and moisture exchange element holder lid 24 approaches or rests against an inside surface of the cap 20. The nebulizer insertion linkage 30 lifts off of the seat at the nebulizer port 18, providing gas flow from the nebulizer port 18 into the enclosure 12. Since nebulizers 50 have varying sizes, the secondary spring 21 compensates for different sizes of nebulizers 50, such that nebulizers 50 with longer insertion tubes will further displace the nebulizer insertion linkage 30 and the secondary spring 21 will respond by compressing once the primary spring 22 has compressed. With the heat and moisture exchange element holder 31 in position close to or against the cap 20, both the upper port 29 of the heat and moisture exchange element holder 31 and the lower port 28 of the heat and moisture exchange element holder 31 are occluded by walls of the enclosure 12, therefore, isolating the heat and moisture exchange element 34 from any gases flowing from the nebulizer 50 or back from the patient port 14. Instead, gases now communicate between the patient port 14, with the lower enclosure port 46, around the nebulizer insertion linkage 30, with the nebulizer port 18, with the lower vent port 15 of the housing, and with the vent circuit communication port 16.

When the nebulizer 50 is removed from the nebulizer port 18, the main spring 22 urges the heat and moisture exchange element holder 31 toward the nebulizer port 18, putting the heat and moisture exchange element 34 back into the circuit while the secondary spring 21 further urges the nebulizer linkage 30 further into the nebulizer port 18, thereby blocking flow of gases in/out of the nebulizer port 18.

As previously stated, the above description and figures represent one exemplary embodiment and the invention is not limited to the mechanical embodiment shown. For example, in other embodiments, insertion of the nebulizer 50 moves walls instead of the heat and moisture exchange element holder 31, selectively blocking/occluding passages and rerouting gases either through the heat and moisture exchange element 34 or around the heat and moisture exchange element 34, without moving the heat and moisture exchange element 34 and holder 31.

Figure 4:
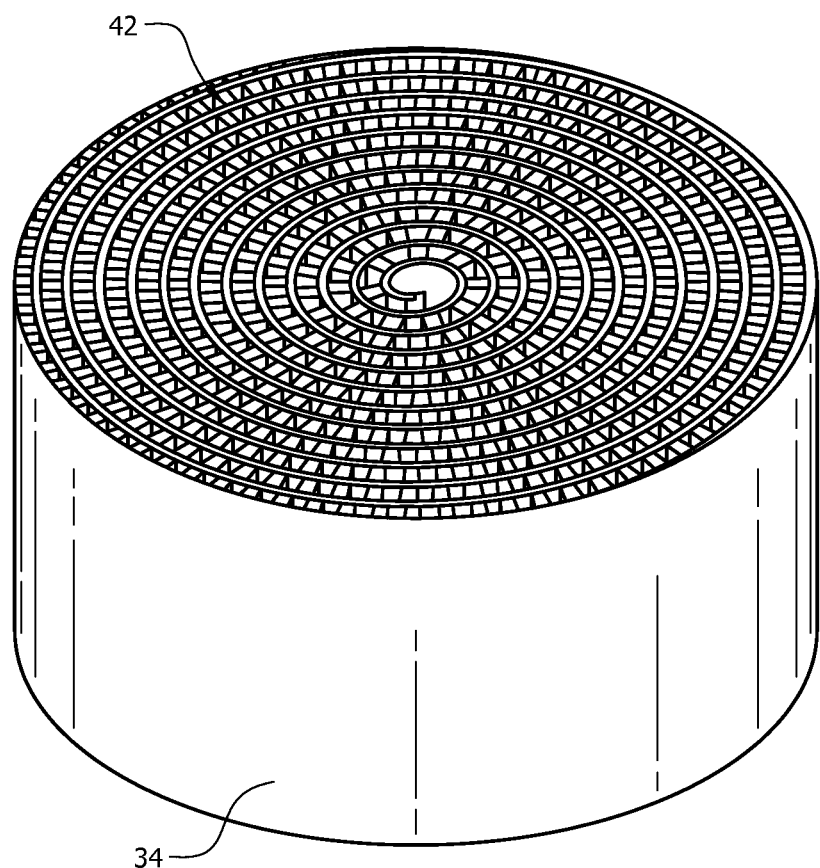
FIG. 4 illustrates a perspective view of an exemplary heat and moisture exchange element.

Referring to FIG. 4, a perspective view of a heat and moisture exchange element 34 is shown. There is no restriction on the size, shape, and composition of the heat and moisture exchange element 34. The heat and moisture exchange element 34 shown in the exemplary figures is one typical example of such. In general, the heat and moisture exchange element 34 is constructed in any way known in the field, for example, by a strip of bacterial filter material that is folded laterally into pleats and bent into a loop so that the folds extend radially as disclosed in U.S. Pat. No. 5,035,236 issued Jul. 30, 1991.

Figure 5:
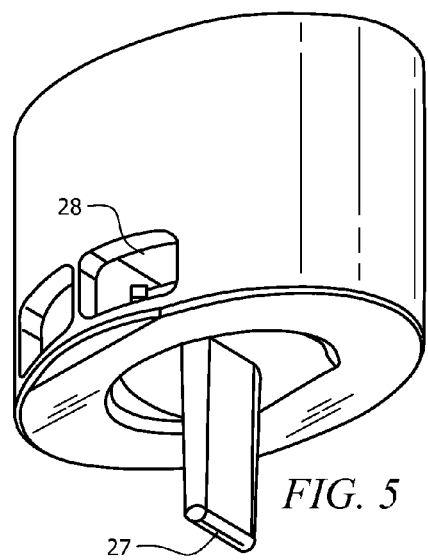
FIGS. 5 and 6 illustrate perspective views of a heat and moisture exchange element holder of the exemplary airway circuit.
Figure 6:
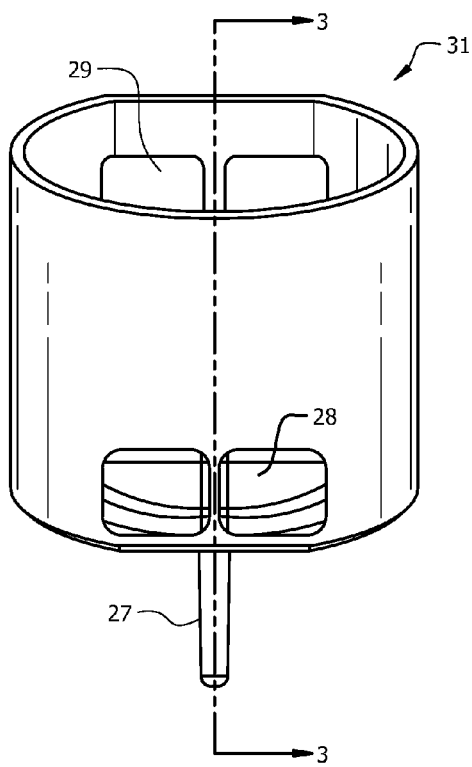

Referring to FIGS. 5 and 6, perspective views of a heat and moisture exchange element holder 31 of the exemplary airway circuit with heat and moisture exchange element 34 are shown. The lower port 28 is open to the vent circuit communication port 14 when the nebulizer 50 is absent from the nebulizer port 18. The upper port 29 is open to the patient port 14 through the upper enclosure port 44 when the nebulizer 50 is absent from the nebulizer port 18. After the nebulizer 50 is inserted into the nebulizer port 18 and the heat and humidity exchange element holder 31 moves away from the nebulizer port 18, both the upper port 29 and the lower port 28 are occluded by the side wall of the enclosure 12. The upper enclosure port 44 is blocked as well, but gases flow in/out of the patient port 14 through the lower enclosure port 46, beneath the heat and humidity exchange element holder 31 and in/out of the vent circuit communication port 16. Since the nebulizer insertion linkage 30 also moves away from the nebulizer port 18, gases and medication from the nebulizer 50 are free to flow into the enclosure and, for example, toward the patient port 14.

Figure 7:
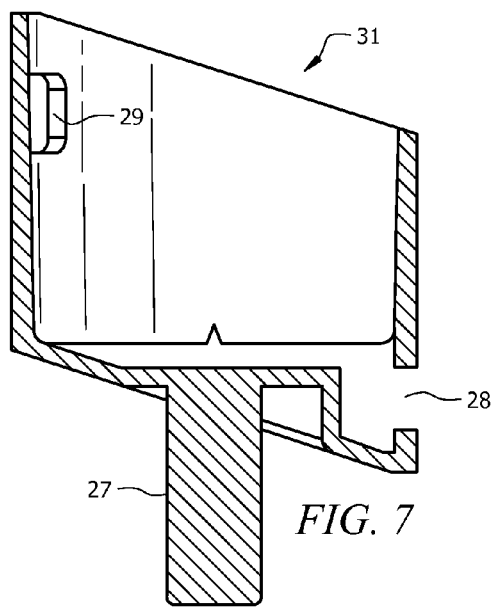
FIG. 7 illustrate a cross sectional view of a heat and moisture exchange element holder of the exemplary airway circuit.

Referring to FIG. 7, a cross sectional view of a heat and moisture exchange element holder 31 of the exemplary airway circuit is shown. When the heat and moisture exchange element 34 is held within the heat and moisture exchange element holder 31, gas flow is possible onto one side of the heat and moisture exchange element 34 through the upper port 29 and gas flow is possible onto the opposite side of the heat and moisture exchange element 34 through the lower port 28.

Equivalent elements can be substituted for the ones set forth above such that they perform in substantially the same manner in substantially the same way for achieving substantially the same result.

It is believed that the system and method as described and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. A patient connector providing heat and humidity exchange, the connector comprising:
    an enclosure having a patient port for connection to a patient circuit, a ventilation communications port for connection to a ventilation circuit, and a nebulizer port for intermittent connection to a nebulizer;
    a heat and moisture exchange element holder having a heat and moisture exchange element contained there within, an upper port in fluid communication with a first side of the heat and moisture exchange element and having a lower port in fluid communication with an opposing side of the heat and moisture exchange element;
    a means for urging, the means for urging urges the heat and moisture exchange element holder towards the nebulizer port;
    a linkage between the nebulizer port and the heat and moisture exchange element such that the linkage blocks the nebulizer port, the patient port is in fluid communications with the upper port and the ventilation communications port is in fluid communications with the lower port allowing fluid communications between the patient port and the ventilation communications port through the heat and moisture exchange element and such that after insertion of a nebulizer into the nebulizer port, the linkage opens the nebulizer port, the patient port is in fluid communications with the nebulizer port and the ventilation communications port allowing fluid communications between the patient port and the ventilation communications port and the nebulizer port.

2. The patient connector of claim 1, wherein the heat and moisture exchange element is fluidly isolated when the nebulizer port is occupied by occlusion of the upper port and the lower port.

3. The patient connector of claim 1, wherein the means for urging is a primary spring.

4. The patient connector of claim 1, wherein the means for urging is a primary spring between an inside surface of the enclosure and an outside surface of the heat and moisture exchange element holder and a secondary spring between an opposing outside surface of the heat and moisture exchange element holder and the linkage, the secondary spring compensating for multiple sizes of nebulizer tips inserted a different times into the nebulizer port.

* * * * *